United States Patent
Kim et al.

(10) Patent No.: US 12,396,915 B2
(45) Date of Patent: Aug. 26, 2025

(54) COMPLEX MASSAGE MACHINE FOR EYES AND NOSE

(71) Applicants: Chang On Kim, Busan (KR); Yong Kim, Busan (KR)

(72) Inventors: Chang On Kim, Busan (KR); Yong Kim, Busan (KR)

(\*) Notice: Subject to any disclaimer, the term of this patent is extended or adjusted under 35 U.S.C. 154(b) by 1007 days.

(21) Appl. No.: 17/299,580

(22) PCT Filed: Dec. 10, 2019

(86) PCT No.: PCT/KR2019/017417
§ 371 (c)(1),
(2) Date: Mar. 3, 2022

(87) PCT Pub. No.: WO2020/149532
PCT Pub. Date: Jul. 23, 2020

(65) Prior Publication Data
US 2022/0218557 A1    Jul. 14, 2022

(30) Foreign Application Priority Data
Jan. 17, 2019    (KR) .......................... 10-2019-0006430

(51) Int. Cl.
*A61H 9/00*  (2006.01)
*A61F 7/00*  (2006.01)
(Continued)

(52) U.S. Cl.
CPC ........... *A61H 9/0078* (2013.01); *A61F 7/007* (2013.01); *A61F 7/12* (2013.01); *A61H 23/02* (2013.01);
(Continued)

(58) Field of Classification Search
CPC .... A61H 39/04; A61H 23/02; A61H 23/0254; A61H 2205/024; A61H 2205/023;
(Continued)

(56) References Cited

U.S. PATENT DOCUMENTS 5,683,436 A * 11/1997 Mendes ............... A61N 5/0603
607/90
2006/0135890 A1 * 6/2006 Tsai ........................ A61H 5/00
601/37

(Continued)

FOREIGN PATENT DOCUMENTS

JP    3115942 U    11/2005
JP    3138513 U    1/2008
(Continued)

*Primary Examiner* — Brandy S Lee
*Assistant Examiner* — Rohan Patel
(74) *Attorney, Agent, or Firm* — NKL LAW; Jae Youn Kim (57) ABSTRACT

An eye & nose multi massager that massages around eyes and inside the nose is proposed. The massager is equipped with a pillow eye mask with fixed bands that cover around eyes; a housing installed to fix the shape of the pillow eye mask; the body of the device installed inside the above housing with the controller to provide options such as vibration, heating, air pressure and other massages to the mask; the rhinitis treatment function inserted through the nose working together with the above body; and a remote controller connected with the panel assembly to manage the options of the body related to the rhinitis treatment function. It's possible to reduce eye fatigue and improve the effects of treatment with the help of thermal massage that works a heat pack if the massager is used.

5 Claims, 7 Drawing Sheets

(51) Int. Cl.
*A61F 7/12* (2006.01)
*A61H 23/02* (2006.01)

(52) U.S. Cl.
CPC ............... *A61F 2007/0006* (2013.01); *A61F 2007/0071* (2013.01); *A61F 2007/0086* (2013.01); *A61F 2007/0096* (2013.01); *A61H 2201/0207* (2013.01); *A61H 2201/0228* (2013.01); *A61H 2201/1604* (2013.01); *A61H 2201/165* (2013.01); *A61H 2201/5082* (2013.01); *A61H 2205/023* (2013.01); *A61H 2205/024* (2013.01)

(58) Field of Classification Search
CPC ...... A61H 2201/5082; A61H 2201/165; A61H 2201/1604; A61H 2201/0228; A61H 2201/0207; A61H 2201/02; A61H 2201/0103; A61F 2007/0004; A61F 2007/0006

See application file for complete search history.

(56) References Cited

U.S. PATENT DOCUMENTS

| | | | |
|---|---|---|---|
| 2006/0200052 A1* | 9/2006 | Lin | A61H 23/0263 601/37 |
| 2013/0158449 A1* | 6/2013 | Juto | A61H 1/00 601/46 |
| 2016/0045277 A1* | 2/2016 | Lin | A61B 34/20 604/93.01 |
| 2019/0380761 A1* | 12/2019 | Catanzaro | A61F 7/123 |

FOREIGN PATENT DOCUMENTS

| | | | |
|---|---|---|---|
| KR | 10-0922277 B1 | 10/2009 | |
| KR | 10-2010-0086188 A | 7/2010 | |
| KR | 10-2013-0053257 A | 5/2013 | |
| WO | WO-2018178197 A2 * | 10/2018 | ............ A61H 21/00 |

* cited by examiner

COMPLEX MASSAGE MACHINE FOR EYES AND NOSE

TECHNICAL FIELD

The present innovation helps to reduce eye fatigue by messaging areas around eyes and treat rhinitis with the help of its thermal massage. Furthermore, the Eye & Nose Multi Massager could heal eye problems such as cataract by removing secretions clogged in interlobular ducts.

BACKGROUND ART

In general, eyes are the main sensory organ of the visual system that helps us to see objects with light stimulation; however, they get easily tired since we live our daily lives with eyes wide open except for sleeping time.

The google-like eye massager from reference 1 has been claimed for earlier application by the applicant and was patented for eye health with a vibrating motor installed inside; a separate vibrating board with several acupressure rods; a switch-type cover on the outermost part of the front frame; multiple through-holes that provide space for acupressure rods of the vibrating board inside the frame; through-holes that fit well with eyes; a compression control band to press through-holes on both sides of the vibrating board.

The Korea's patent gazette (No. 10-1054552) from the applicant shows that the device stimulates acupuncture points around eyes with the help of vibrating motors, air tubes, and heating films to optimize eye health and relieve psychological stress; provides relieving music to further improve the effects of acupressure therapy; fits with eyes due to its curved design to control the intensity of the massager depending on their eye shapes and taste with the help of its simple method of use for young and old in their daily lives; and eye holes on both sides installed with mutually attached bands. This specially designed device consists of the outer skin made of elastic materials; the inner skin that physically contacts the rear surface of the outer skin with the same shape and material to the outer skin; heating films with heating wires inside and installed inside between the outer and inner skin, however formed like the outer one; an air tube installed between heating films and the outer skin and equipped with the air entrance connected to an air pump for swelling and contraction; a set of vibrating motors that vibrate the outer skin installed between the above outer skin and each sides of the outer skin; an inner housing and outer housing installed between the air tube on the front and the outer skin that cover the vibrating motor; a protective cover that embraces the outer housing installed in the front of the outer housing; an air pump that connects the heating wire of the above heating films, vibrating motor and air tube while providing air through the air tube inside; a pillow eye pad made of elastic materials on the above inner and outer edges and fits well with eyes; and a built-in remote controller with the power supply unit and music source device that supply power through heat wires and the vibrating motor; and an earphone that transmits music on each side of the above outer skin provided by the music source device.

However, we have more and more rhinitis patients due to environmental pollution and increased production of air pollutants. Rhinitis is irritation and inflammation of the mucous membrane inside the nose, and the most common kind of rhinitis is acute or chronic rhinitis, viral rhinitis caused by the common cold, and allergic rhinitis.

Once you are infected with rhinitis, you are highly likely to suffer breathing problems and other severe accompanying symptoms such as headache and loss of concentration. In particular, this could put children at high risk of choking in severe cases.

Therefore, the applicant has invented this device that massage eyes and treat rhinitis since the necessity of the multi massage device is well recognized.

Detailed Description of the Invention

Technological Challenges

In order to tackle issues related to previous technologies, this present invention has adopted the new technology with the body that massages around eyes equipped with multiple options such as vibration, acupres sure and heating and combined with other functions to heal rhinitis by massaging the inside of the nose with its thermal function. Overall, the Eye & Nose Multi Massager aims to improve treatment outcomes of eye and nose symptoms by providing eye massage and nose cure heating massage.

Task-Solving Skills

As one of the ways to tackle the issues, the present invention has equipped with a pillow eye mask with fixed bands that cover around eyes; a housing installed to fix the shape of the pillow eye mask; the body of the device installed inside the above housing with the controller to provide options such as vibration, heating, air pressure and other massages to the mask; the rhinitis cure function inserted through the nose working together with the above body; and a remote controller connected with the panel assembly to manage the options of the body related to the rhinitis cure function.

In addition, it is equipped with the base housing inside the front of the outer skin helps the shape of the pillow eye mask and equipped with the control section; a protective cover installed in the front of the base housing that is separated on both side of the base plate and hingedly connected to both sides of base plates while a pair of flow side plates are installed to fold at a predetermined angle.

Furthermore, the rhinitis cure function has inserted power lines inside the easily-bent flexible tubes; an electric connecter combined with the panel assembly of the body at the rear end of the above flexible tubes with the control section; and a pair of heating units that emit heat inside of the nose.

Also, the above heating unit includes a pair of carbon fiber heating wires that generate heat through power wires; a heating insertion hole inserted through the nose that has the above carbon fiber heating wires inside; and the bimetal thermometer used for measuring and controlling temperature of the carbon fiber heating wires that emit heat inside the heating insertion hole.

Not only that, the rhinitis cure function gets closer to the inner wall of the nose through the heating unit designed to provide air pressure while swelling and contracting to a limited volume; works as a heat pack inside the nose with auxiliary air tubes built in the flexible tubes to provide air pressure between the remote controller's air pump and heating unit; and includes an airbag that swells and contracts while being connected to auxiliary air tubes inside the heating insertion hole of the heating unit.

Effects of the Invention

The present invention, Eye & Nose Multi Massager, promotes the circulation of the blood and skin vitality with the help of such options as vibration, air pressure and heating massage by relieving skin tension that doesn't circulate well due to clogged nerves, blood vessels, lacrimal glands, tear dusts as well as stiff muscles around eyes; dissolves dust on the eyeballs and fat secretions hardened inside the eyelids with the help of heating; emits secretions with the air pressure message that lets tears flow out of the eyes; clears eyes with the help of circulation of tears; and improves eyesight benefitting from relieved dry eye symptoms and lower eye pressure.

In addition, if you expose heating to the nose, it helps to promote the circulation of interlobular ducts and subsequently treat cataracts.

Also, both ends of the housing that constitute the body of the device work with hinges so that you can improve the benefits of message regardless of shape or size of the face.

BEST MODE FOR CARRYING OUT THE INVENTION

Hereinafter, the Eye & Nose Multi Massager of the present invention will be described in detail according to the best modes shown in the drawings.

Figure 1:
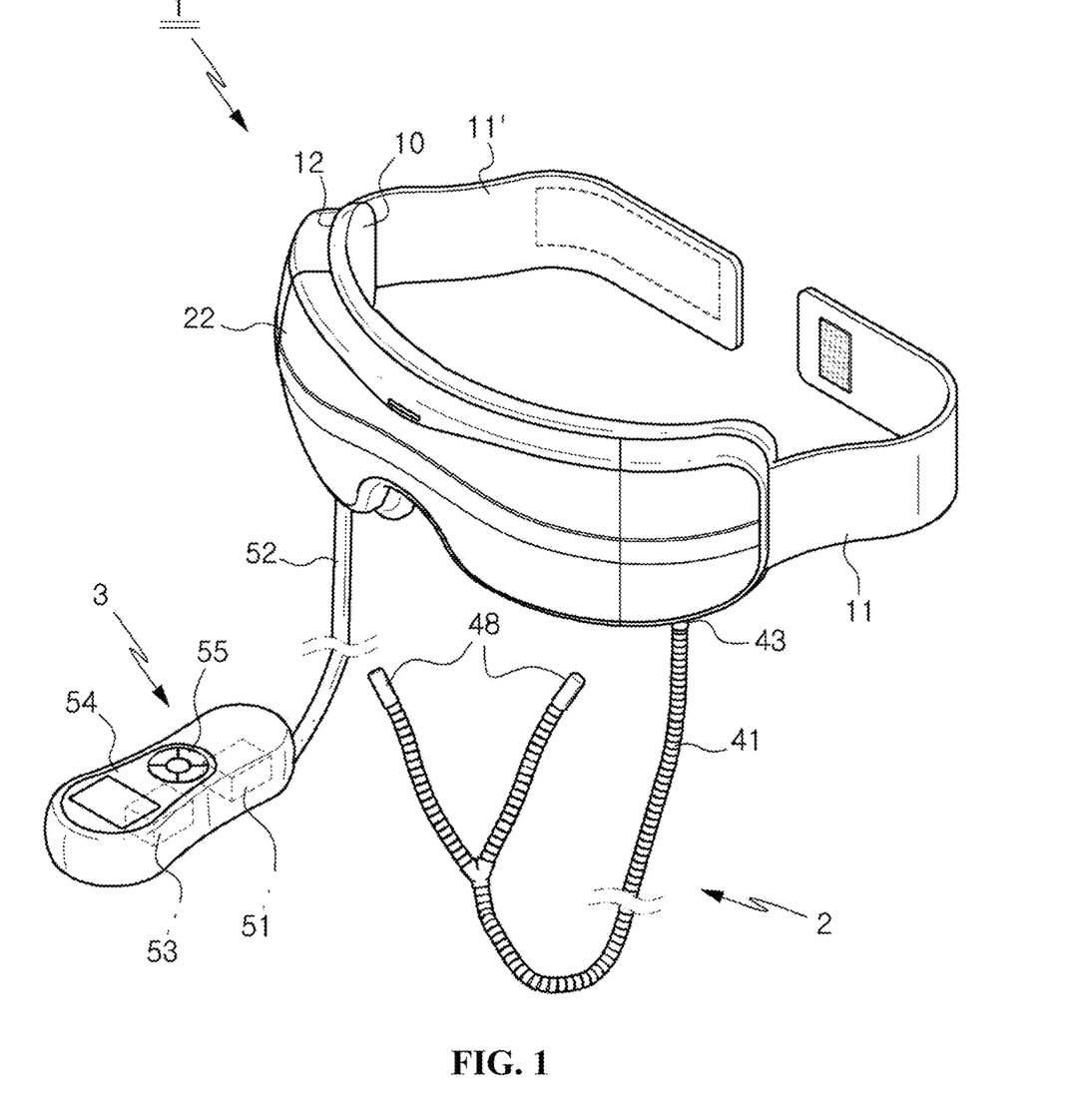
FIG. 1 is a perspective view showing an embodiment of Eye & Nose Multi Massager according to the present invention.
Figure 2:
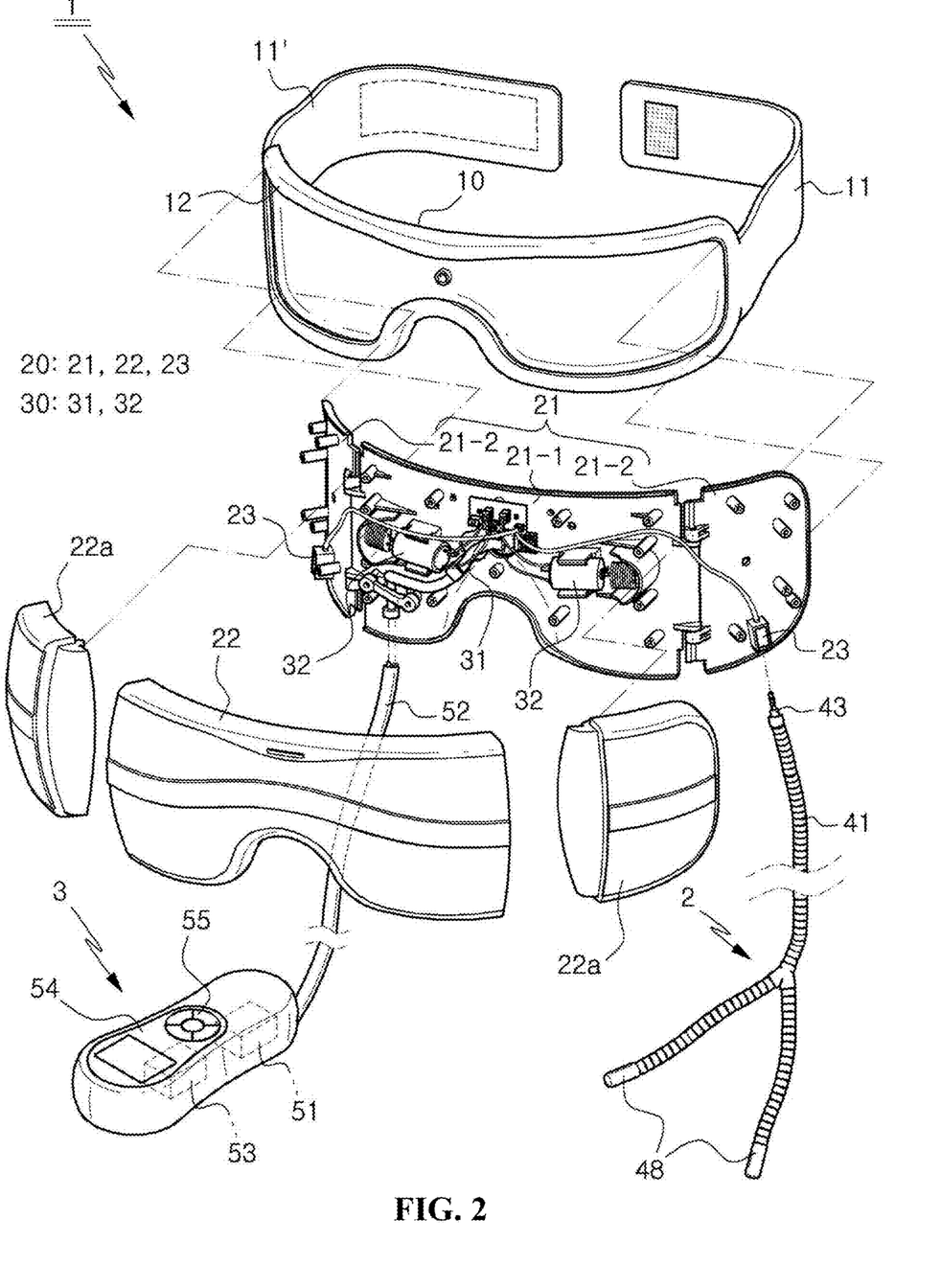
FIG. 2 is an exploded skew drawing showing an embodiment of Eye & Nose Multi Massager according to the present invention.

FIG. 1 is a perspective view showing an embodiment of the Eye & Nose Multi Massager according to the present invention while FIG. 2 is a perspective view showing an embodiment of the Eye & Nose Multi Massager according to the present invention.

The present invention has equipped with a pillow eye mask (10) with fixed bands (11,11') that cover around eyes; a housing (20) installed to fix the shape of the mask (10) ; the body (1) of the device installed inside the above housing (20) with the control section (30) to provide options such as vibration, heating, air pressure and other massages to the cushion eye mask (10); the rhinitis cure function (2) inserted through the nose while working together with the above body (1) the device; and a remote controller (3) connected with the control section (30) to manage the options of the body (1) of the device and the rhinitis cure function (2).

The above pillow eye mask (10) is equipped with the outer skin (12) that covers around eyes; an acupressure pad (13) designed to massage around eyes while swelling and contracting with the help of air pressure inside the outer skin (12); and carbon fiber films (14) that emit heat with its heating function.

Furthermore, fixed bands (11,11') are made of elastic materials on each side of the outer skin (12) and have hook & loop fasteners at the end of the pillow eye mask (20) that could easily connect each other.

The above housing (20) is equipped with the base housing (21) installed inside the front of the outer skin to fix the shape of the pillow eye mask (10) as well as the control unit (30); and a protective cover installed in the front of the base housing (21) to develop an aesthetic sense while protecting the control section (30) installed in the above base housing (21).

Also, the base housing (21) separated on both side of the base plate is hingedly connected to both sides of base plates (21-1) to form a pair of flow side plates (21-2) are installed to fold at a predetermined angle.

Figure 3:
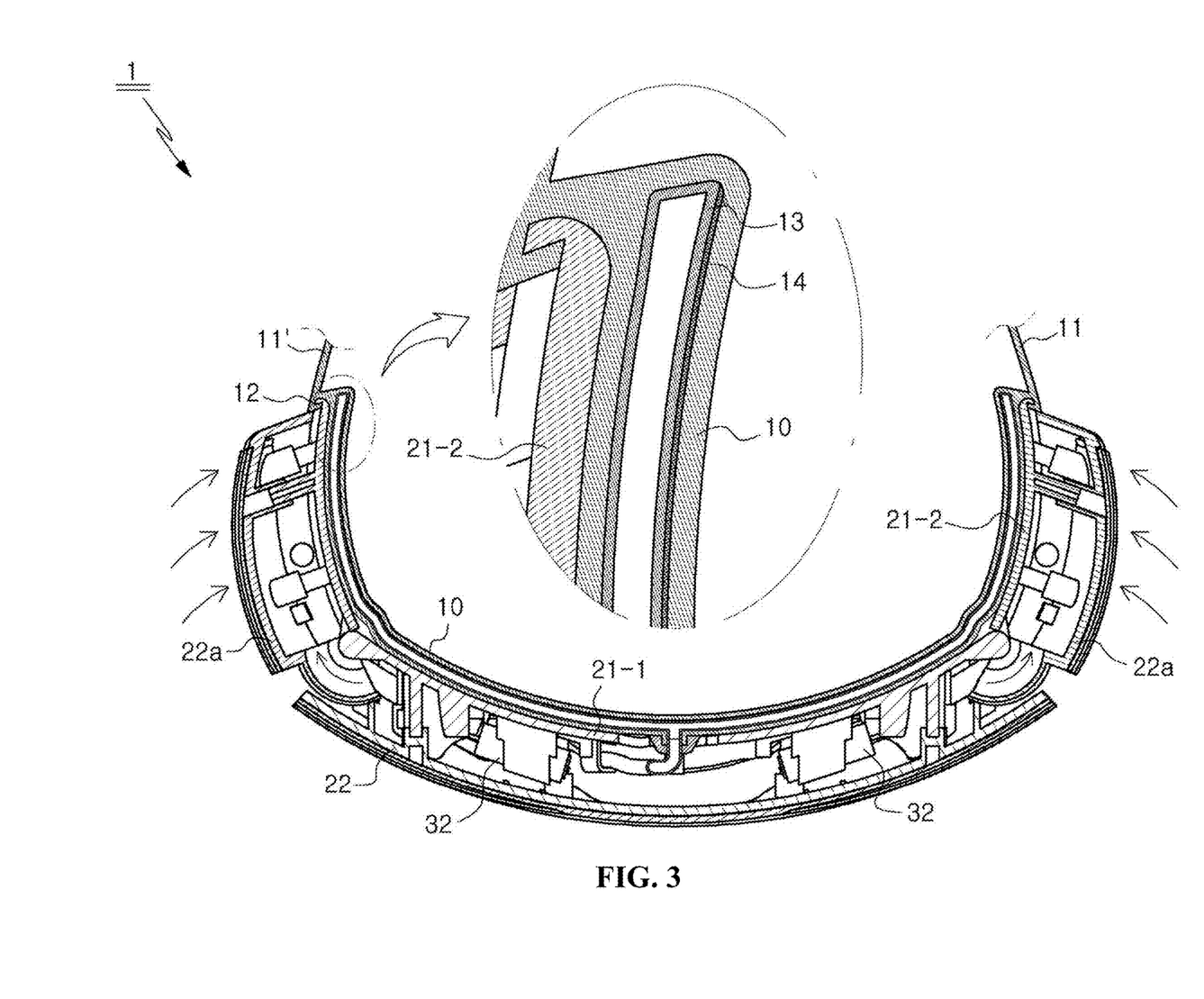
FIG. 3 is a floor section view showing an embodiment of the body of the eye massager of Eye & Nose Multi Massager according to the present invention.

As shown in FIG. 3, the base housing (21) fits well with the user's face with a pair of flow side plates (21-2) of the base plate (21-1) that fold at a predetermined angle when you wear it around eyes with fixed bands (11,11') connected to each other; solves problems for users with small faces could fit with both ends of the device since it fits closely with the front and sides of faces regardless of their shape or size; and completely gives comfort to faces when you wear the device tightened with fixed bands (11,11').

Just like the separate structure of the base housing (21), the above protective cover (22) has flow protective cover (22a) to form separated on both side of the base plate to work with hinges coupled with flow side plates 21-2).

The above control section (30) is installed with the circuit board (31) that receives signals from the remote controller (3) from the upper center of the base housing (21); a vibrating motor (32) on both sides for vibration, heating and air pressure options to both sides of the above circuit board (31); and both the vibrating motor and carbon fiber films (12) that are connected to each other electrically to control the operation in the circuit board (31).

Figure 4:
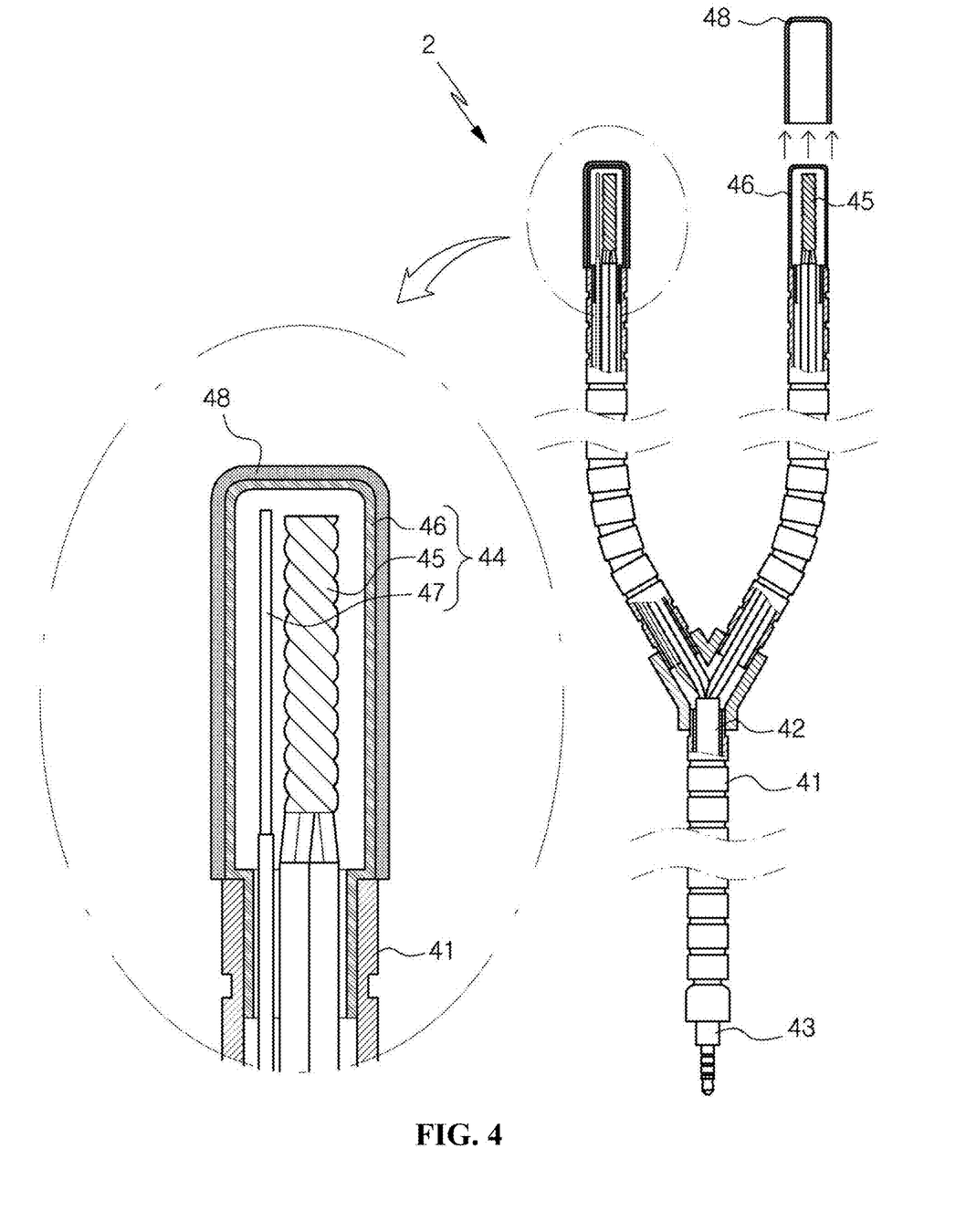
FIG. 4 is a front section view showing an embodiment of the rhinitis cure function massager of Eye & Nose Multi Massager according to the present invention.

The above rhinitis cure function (2) has easy-to-bend flexible tubes (41); power lines (42) inserted inside of the above flexible tubes (41); connectors (43) formed to connect the above circuit board (31) of the control section (30) at the rear end of the above flexible tubes (41) with the electronic power lines; and a pair of heating unit (44) that emit heat inside the nose.

Also, the above heating unit (44) includes a pair of carbon fiber heating wires (45) that generate heat through power wires (42) ; a heating insertion hole (46) inserted through the nose that has the above carbon fiber heating wires (45) inside; and the bimetal thermometer (47) used for measuring and controlling temperature of the carbon fiber heating wires (45) that emit heat inside the heating insertion hole (46).

Furthermore, the above heating unit (44) can be provided with more replaceable silicone covers (48) to the heating insertion hole (46) to prevent infections through bacteria.

The above heating insertion hole (46) may replace the heating insertion hole (46) with have carbon fiber heating lines (45) made of silicone without the use of separate silicone covers (48).

Such rhinitis cure function (2) can be used by simply connecting the sockets of the body (1) to the connecter while the flexible tube (41) with the heating unit (44) is inserted through the nose without any difficulties Furthermore, if you choose the rhinitis cure function in the remote controller (3), the carbon fiber heating wires (45) emit heat to provide thermal massage inside the nose through the heating insertion hole and subsequently help heal rhinitis.

Figure 5:
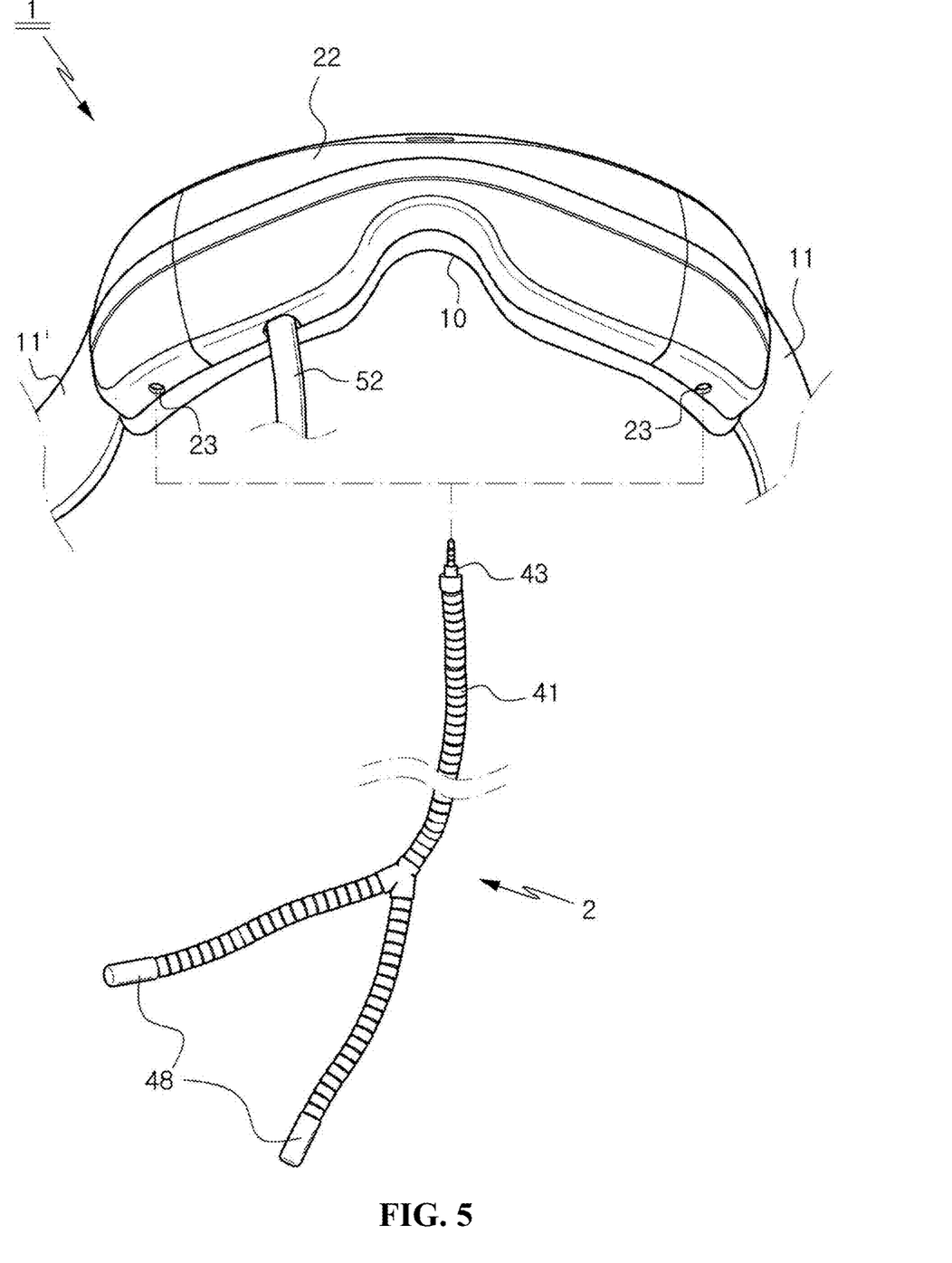
FIG. 5 is a drawing showing an embodiment of the connecting components of Eye & Nose Multi Massager according to the present invention.

As shown in FIG. 5, both sides or one side of the base housing (21) is advised to have the panel assembly (23) that connects the connector with the rhinitis cure function (2) with the circuit board (31) electronically.

The above built-in remote controller has the power supply unit (51) that provides power to the vibrating motor (32), carbon fiber films (14), rhinitis treatment function (2) electronically connected with the circuit board (31) of the control section (30); an air tube (52) that lets air in and out of the acupuncture pad (13), an air pump that provides air through the above air tube (52); the operation unit (54) that control temperature combined with the above body (1) and rhinitis treatment function (2) individually or in combination.

The above operation unit (54) has modes of heating, acupressure, and vibration massage, as well as rhinitis treatment function (1) that could operate individually; and control buttons (55) that allow the use of multiple options at the same time for a certain period of time.

Hereinafter, Eye & Nose Multi Massager of the present invention will be described in detail based on its operation shown in the drawings.

Figure 6:
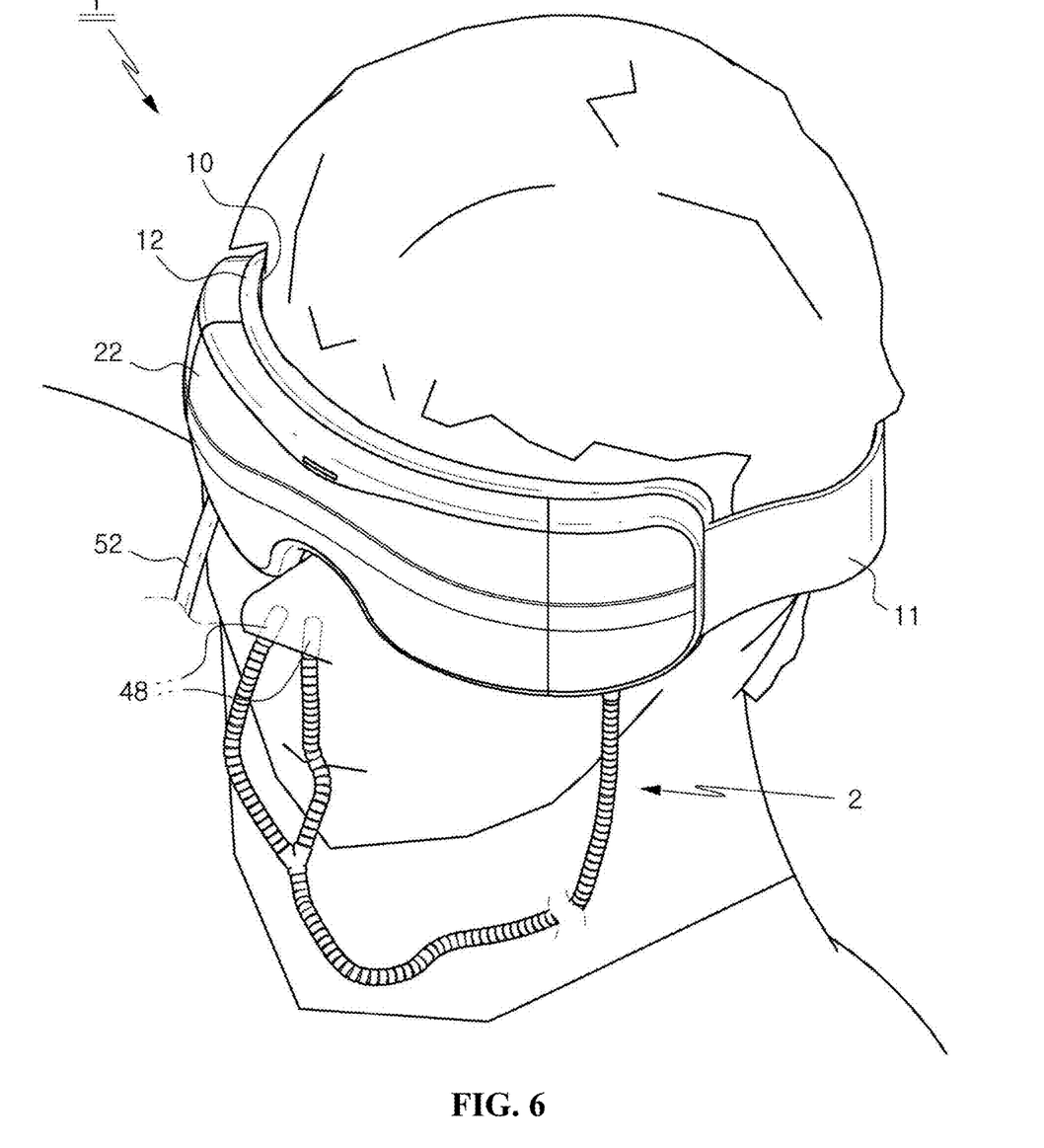
FIG. 6 is a drawing showing an embodiment of the Eye & Nose Multi Massager according to the present invention during use.

Refer to FIG.6, you can easily wear the device by putting it close to around eyes while connecting each side of fixed bands (11,11') to fit the body (1) with eyes. Furthermore, such options as heating, acupressure, and vibration massage are provided through the operation unit (54) of the remote controller (3) individually or in combination with the help of the combination mode designed to operate for a certain period of time for eye massage.

The present invention is separated on both side of the housing (20) installed in the control section (30) that support the pillow eye mask (10); has a pair of flow side plates (21-2) of the base plate (21-1) that fold at a predetermined angle; and fits the face with the flow side plates (21-2) to give comfort to users.

The previous eye massager of the present applicant is originally designed to have the all-in-one pillow eye mask (10) with the built-in base housing (21) that works as frames, resulting in pain due to the inconvenience of tightened fixed bands since both ends of the pillow eye mask (10) don't fit well with the side of the face. However, the present invention has separated flow side plates (21-2) installed to fold at a predetermined angle in the previous both sides of the base plate; fits well with sides of faces regardless of their shape or size; and completely gives comfort to faces without causing any pain or inconveniences.

Furthermore, this present invention can simply connect the rhinitis treatment function (2) with the body (1) while providing both eye and thermal massage inside the nose.

Once the rhinitis treatment function (2) is to connect the connecter (43) of the rhinitis treatment function (2) with the panel assembly (23) formed below the base housing (21) of the body (1) of the device, enabling the use of the body (1) of the device together, thermal massage is provided inside the nose through the controller (54) of the remote controller (3).

The above rhinitis treatment function (2) has a pair of heating unit (44) inserted inside the nose formed inside of the above flexible tubes (41); and the flexible tubes (41) with the heating unit (44) inserted through the nose without any difficulties.

The above heating unit (44) includes a heating insertion hole (46) inserted through both sides of the nose that has the above carbon fiber heating wires (45) inside while a pair of carbon fiber heating wires (45) generate heat inside of the heating insertion hole (46) through the remote controller (3), resulting in improved effects of rhinitis treatment thanks to thermal massage.

The above heating insertion hole (46) on the circumferential external surface of the carbon fiber heating lines (45) can be washed easily and replaced with its separate silicone covers (48) to stay clean for personal hygiene.

The present invention, the Eye & Nose Multi Massager, promotes the circulation of the blood and skin vitality with the help of such options as vibration, air pressure and heating massage by relieving skin tension that doesn't circulate well due to clogged nerves, blood vessels, lacrimal glands, tear dusts as well as stiff muscles around eyes; dissolves dust on the eyeballs and fat secretions hardened inside the eyelids; emits secretions with the air pressure message that lets tears flow out of the eyes; clears eyes with the help of circulation of tears; and improves eyesight befitting from relieved dry eye symptoms and lower eye pressure. In addition, if you expose eating to the nose, it helps to promote the circulation of interlobular ducts and subsequently treat cataracts.

Not only that, the rhinitis treatment function (2) of the Eye & Nose Multi Massager gets closer to the inner wall of the nose through the heating unit (44) designed to provide air pressure while swelling and contracting to a limited volume, leading to improved effects of the treatment by heating inside the nose.

Figure 7:
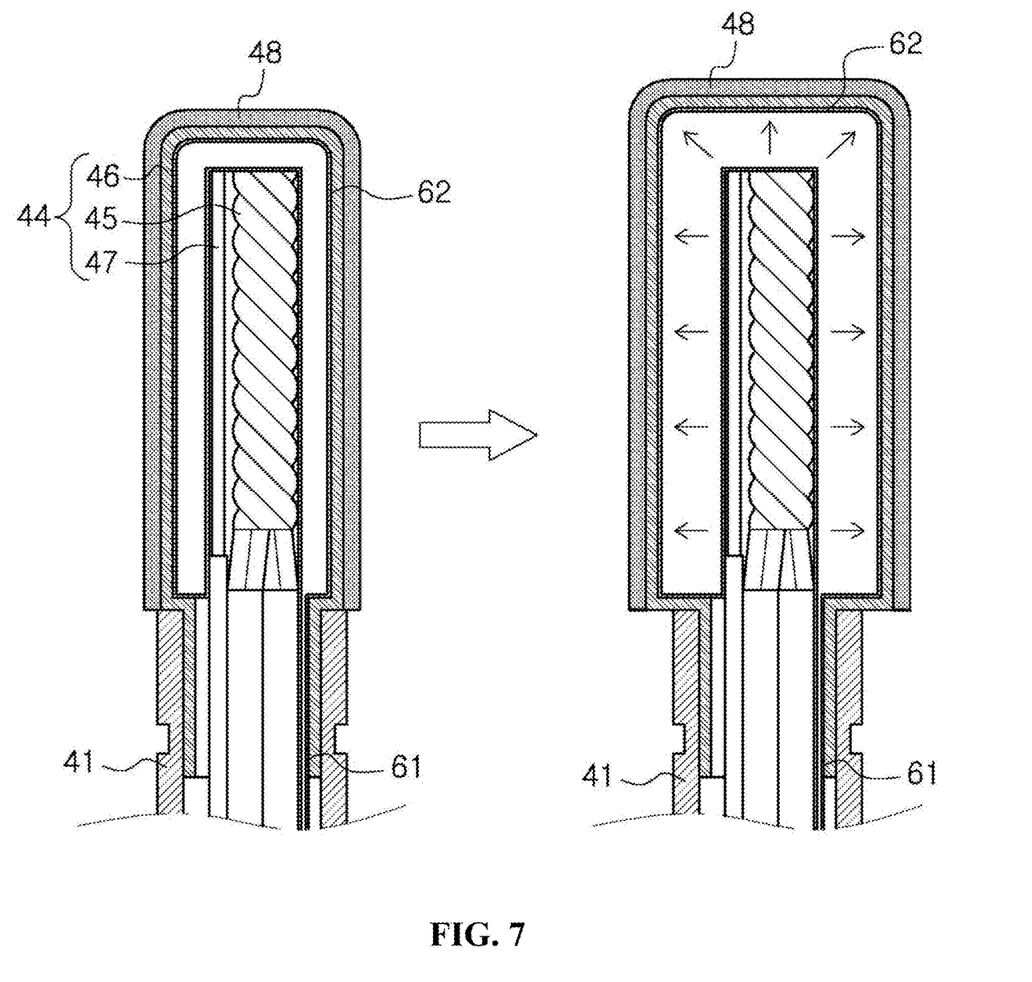
FIG. 7 is a drawing showing the best mode of the rhinitis cure function of Eye & Nose Multi Massager according to the present invention.

Refer to FIG. 7, it works as a heat pack with auxiliary air tubes built in the flexible tubes (41) to provide air pressure between the remote controller(3)'s air pump (53) and heating unit (44); and includes an airbag (62) that swells and contracts while being connected to auxiliary air tubes (61) inside the heating insertion hole (46) of the heating unit (44).

The above airbag (62) is installed in a cylindrical structure that penetrates the carbon fiber heating wires (45); and swells and contracts inside the heating insertion hole (46).

The heating insertion hole (46) made of soft synthetic resin or silicone could swell and contract to a predetermined volume while responding to the airbag (62); and works a heat pack while closely contacting inside of the nose, improving the symptoms of rhinitis.

As described above, the best modes of the present invention have been described in detail, but various modifications could be applied within the scope of this technology. Therefore, the technical scope of the present invention is not limited to the best modes mentioned above, and recognize the technologies of the claims described below and other technologies equivalent to those technologies.

INDUSTRIAL APPLICABILITY

The present invention, the Eye & Nose Multi Massager, is the body of eye massager that provides vibration and heating around eyes with the rhinitis treatment function that massages inside the nose with the help of its thermal option, so it is industrially applicable to the treatment of eye and nose problems with the use of the combination of eye and nose massage.

The invention claimed is:
1. An eye and nose multi massager comprising:
   a body including: a pillow eye mask with fixed bands, the pillow eye mask configured to cover around eyes of a user; a housing installed to fix a shape of the pillow eye mask; and a controller installed inside the housing to provide options including vibration, heating, and air pressure massages to the pillow eye mask;
   a rhinitis treatment hose configured to be inserted through a nose of the user and configured to work together with the body;

a remote controller connected with the controller to manage the options of the body; and a panel assembly connecting the rhinitis treatment hose to one side of the body, wherein the rhinitis treatment hose has flexible tubes, power lines inserted inside of the flexible tubes, connectors to electronically connect a circuit board of the controller with the panel assembly at a rear end of the flexible tubes, and a pair of heaters configured to emit heat inside the nose.

2. The massager of claim 1, wherein the housing is inserted into an inner front side of the pillow eye mask to maintain the shape of the pillow eye mask, and the housing includes a base housing in which the controller is installed, and a protective cover installed in a front side of the base housing, and wherein the base housing includes a base plate and a pair of flow side plates that are hingedly connected to both sides of the base plate and are configured to fold at a predetermined angle.

3. The massager of claim 1, wherein each of the pair of heaters includes; a carbon fiber heating wire that generates heat through power wires; a heating insertion hole configured to be inserted through the nose, the heating insertion hole having the carbon fiber heating wire disposed inside thereof; and a bimetal thermometer used for measuring and controlling temperature of the carbon fiber heating wire that emits heat inside the heating insertion hole.

4. The massager of claim 1, wherein each of the pair of heaters includes a heating insertion hole configured to be inserted through the nose, wherein the remote controller includes an air pump and is configured to control the air pump, wherein the rhinitis treatment hose further includes auxiliary air tubes built in the flexible tubes and an airbag that swells or contracts while being connected to the auxiliary air tubes inside the heating insertion hole of each of the pair of heaters, wherein the auxiliary air tubes are configured to provide air pressure between the air pump of the remote controller and the heater such that the rhinitis treatment hose is configured to get closer to an inner wall of the nose through the pair of heaters designed to provide the air pressure while swelling or contracting to a volume, serving as a heat pack to the inner wall of the nose.

5. The massager of claim 3, wherein the remote controller includes an air pump and is configured to control the air pump, wherein the rhinitis treatment hose further includes auxiliary air tubes built in the flexible tubes and an airbag that swells or contracts while being connected to the auxiliary air tubes inside the heating insertion hole of each of the pair of heaters, wherein the auxiliary air tubes are configured to provide air pressure between the air pump of the remote controller and the heater such that the rhinitis treatment hose is configured to get closer to an inner wall of the nose through the pair of heaters designed to provide the air pressure while swelling or contracting to a volume, serving as a heat pack to the inner wall of the nose.

* * * * *